(12) United States Patent
Pember et al.

(10) Patent No.: US 9,945,817 B2
(45) Date of Patent: Apr. 17, 2018

(54) SPECIALLY DESIGNED PHASED ARRAY TRANSDUCER FOR THE INSPECTION OF FASTENER HOLES AND ADJACENT STRUCTURE WITHOUT THE REMOVAL OF THE FASTENER

(71) Applicant: NORTHROP GRUMMAN SYSTEMS CORPORATION, Falls Church, VA (US)

(72) Inventors: William H. Pember, Palm City, FL (US); Kevin L. Boyd, Melbourne, FL (US); Kevin H. Cook, East Farmingdale, NY (US); Chris Famighetti, Melbourne, FL (US); Robert D. Fidnarick, Seaford, NY (US); John Munyak, Nesconset, NY (US); John D. Weir, Huntington, NY (US)

(73) Assignee: Northrop Grumman Systems Corporation, Falls Church, VA (US)

( * ) Notice: Subject to any disclaimer, the term of this patent is extended or adjusted under 35 U.S.C. 154(b) by 372 days.

(21) Appl. No.: 14/818,138

(22) Filed: Aug. 4, 2015

(65) Prior Publication Data

US 2017/0038341 A1 Feb. 9, 2017

(51) Int. Cl.
*G01N 29/26* (2006.01)
*G01N 29/06* (2006.01)
*B64F 5/60* (2017.01)

(52) U.S. Cl.
CPC ........... *G01N 29/0654* (2013.01); *B64F 5/60* (2017.01); *G01N 29/0609* (2013.01);
(Continued)

(58) Field of Classification Search
CPC ........... G01N 29/0654; G01N 29/0609; G01N 29/262; G01N 2291/106; G01N 2291/0289; G01N 2291/023; B64F 5/60
(Continued)

(56) References Cited

U.S. PATENT DOCUMENTS 3,810,385 A * 5/1974 McFaul ............... G01B 17/04
310/327
3,977,236 A * 8/1976 Raatz, Jr. ........... G01N 29/0645
73/614
(Continued)

FOREIGN PATENT DOCUMENTS

CN 104280458 A 1/2015

OTHER PUBLICATIONS

Ultrasonic Phased array Inspection for an Isogrid structural element with cracks, Roth et al., NASA/TM Mar. 2010.*
(Continued)

*Primary Examiner* — J M Saint Surin
(74) *Attorney, Agent, or Firm* — John A. Miller; Shumaker, Loop & Kendrick, LLP

(57) ABSTRACT

A phased array transducer for inspecting a fastener hole and adjacent structure to identify defects and determine hole integrity without removing the fastener from the hole. The phased array transducer includes a plurality of transducer elements, where one of the transducer elements is used to align the transducer to the hole, one group of the remaining transducer elements inspects the entire thickness of the structure at one side of the fastener and another group of the remaining transducer elements inspects the entire thickness of the structure at an opposite side of the fastener.

18 Claims, 3 Drawing Sheets

(52) U.S. Cl.
CPC ..... *G01N 29/262* (2013.01); *G01N 2291/023* (2013.01); *G01N 2291/0289* (2013.01); *G01N 2291/106* (2013.01)

(58) Field of Classification Search
USPC .......................................................... 73/628
See application file for complete search history.

(56) References Cited

U.S. PATENT DOCUMENTS

| | | | |
|---|---|---|---|
| 4,712,428 A | 12/1987 | Ishii et al. | |
| 5,156,050 A * | 10/1992 | Schmid | B06B 1/0681 |
| | | | 73/628 |
| 5,460,047 A | 10/1995 | Jacobson | |
| 7,328,619 B2 * | 2/2008 | Moles | G01N 29/0609 |
| | | | 73/598 |
| 7,730,784 B2 | 6/2010 | Georgeson et al. | |
| 8,181,524 B2 | 5/2012 | Hara et al. | |
| 8,616,062 B2 | 12/2013 | Kono et al. | |
| 8,914,244 B2 | 12/2014 | Kollgaard et al. | |
| 8,973,441 B1 | 3/2015 | Nelson et al. | |
| 8,997,571 B2 | 4/2015 | Someda et al. | |
| 2007/0056375 A1 * | 3/2007 | Akdeniz | G01L 5/243 |
| | | | 73/649 |
| 2009/0178466 A1 * | 7/2009 | Ethridge | G01N 29/07 |
| | | | 73/1.86 |
| 2014/0283612 A1 * | 9/2014 | Williams | G01N 29/24 |
| | | | 73/633 |
| 2014/0352438 A1 | 12/2014 | Scaccabarozzi et al. | |
| 2015/0000409 A1 | 1/2015 | Waedekin et al. | |
| 2015/0053015 A1 | 2/2015 | Sarr et al. | |

OTHER PUBLICATIONS

Phased Array Application for Aircraft Maintenace Fastener-hole inspection, Neau et al.*
Li, Minghui, et al. "Ultrasound Nondestructive Evaluation (NDE) Imaging with Transducer Arrays and Adaptive Processing" SENSORS, ISSN 1424-8220, 2012, vol. 12, pp. 42-54.
Furuhata, T. et al. "Array-Driven Ultrasonic Microactuators" IEEE 1991, pp. 1056-1059.

* cited by examiner

SPECIALLY DESIGNED PHASED ARRAY TRANSDUCER FOR THE INSPECTION OF FASTENER HOLES AND ADJACENT STRUCTURE WITHOUT THE REMOVAL OF THE FASTENER

BACKGROUND

Field

This invention relates generally to a phased array transducer for inspecting a fastener hole in a structure and, more particularly, to a phased array transducer for inspecting a fastener hole in a structure without removing the fastener, where the transducer includes a plurality of transducer elements that are scanned to image the entire thickness of the structure.

Discussion

For many industries, such as the aerospace and aircraft industries, the structural integrity of many vehicle and system components is important. Thus, it is very important in those industries that reliable techniques are available to examine the integrity of the structural components, such as the skin of the aircraft to ensure that the aircraft does not suffer from structural failure when in flight. Therefore, various techniques have been developed for the non-invasive and non-destructive analysis of different structural components and materials to detect for wear, fatigue, corrosion, cracking, etc. in the aircraft and other industries.

One known technique for inspecting a component for defects employs an electromagnetic coil that induces eddy currents in the component. The complex impedance in the coil changes as the eddy current encounters defects in the component, which can be observed on an oscilloscope. Other non-destructive inspection techniques are also known to those skilled in the art.

Most aircraft and other structural components employ fasteners, such as bolts, rivets, structural pins, etc., to hold an assembly of component layers or parts together. When a structure is loaded with these types of fasteners, high stress points are often created that can crack the structure at the fastener locations. For example, after years in service, corrosion often occurs around an opening for a fastener because the fastener is often made of steel and the part is often made of aluminum.

The current techniques for inspecting the area around the hole that a fastener is inserted usually require that the fastener be removed from the structure, such as by drilling out the fastener. An inspection probe is then inserted into the hole and manipulated so that the entire thickness of the component around the hole is inspected. The removal of the fastener can result in tremendous damage to the fastener, nut, finishes and structure adding cost to the inspection process. Further, many structures require disassembly, particularly in the case of multilayer structures that require all layers to be inspected not just the outer layers. In the case of sealed laminate aircraft structures, such as an aircraft keel beam, the removal of the keel beam requires that the aircraft be shored up to support the existing structure and load transfer due to the keel beam structure being removed. Known inspection processes also often require expensive tooling, which must be specially designed, therefore adding additional cost to the inspection process.

One known inspection system that does not require the fastener to be removed from the hole is known in the art as an automated fastener-hole imaging system (AFIS). The AFIS employs a phased array ultrasonic probe, but requires an expensive alignment mechanism to rotate the probe around the fastener. Further, the AFIS needs to be adjusted every time a different fastener size is encountered, thus making the AFIS impractical for many applications involving multi-size fasteners or holes. Additionally, the AFIS needs to be set up and adjusted every time a different fastener hole is be inspected, which makes the inspection process using the AFIS both time-consuming, labor intensive and, in many cases, impractical. Thus, there is a need in the art for an inspection system for inspecting fastener holes while the fastener is still positioned in the hole that is cost effective, less complicated, more versatile, less labor intensive, etc.

SUMMARY

The present disclosure describes a phased array transducer for inspecting a fastener hole and adjacent structure to identify defects and determine hole integrity without removing the fastener from the hole. The phased array transducer includes a plurality of transducer elements, where one of the transducer elements is used to align the transducer to the hole, one group of the remaining transducer elements inspects the entire thickness of the structure at one side of the fastener and another group of the remaining transducer elements inspects the entire thickness of the structure at an opposite side of the fastener.

Additional features of the present invention will become apparent from the following description and appended claims, taken in conjunction with the accompanying drawings.

DETAILED DESCRIPTION OF THE EMBODIMENTS

The following discussion of the embodiments of the invention directed to a phased array transducer that is capable of inspecting a fastener hole without removing the fastener is merely exemplary in nature, and is in no way intended to limit the invention or its applications or uses. For example, the discussion herein refers to the transducer as being used to inspect fastener holes in aircraft components. However, as will be appreciated by those skilled in the art, the phased array transducer of the invention will have application for inspecting fastener holes of components used in many other industries.

Figure 1:
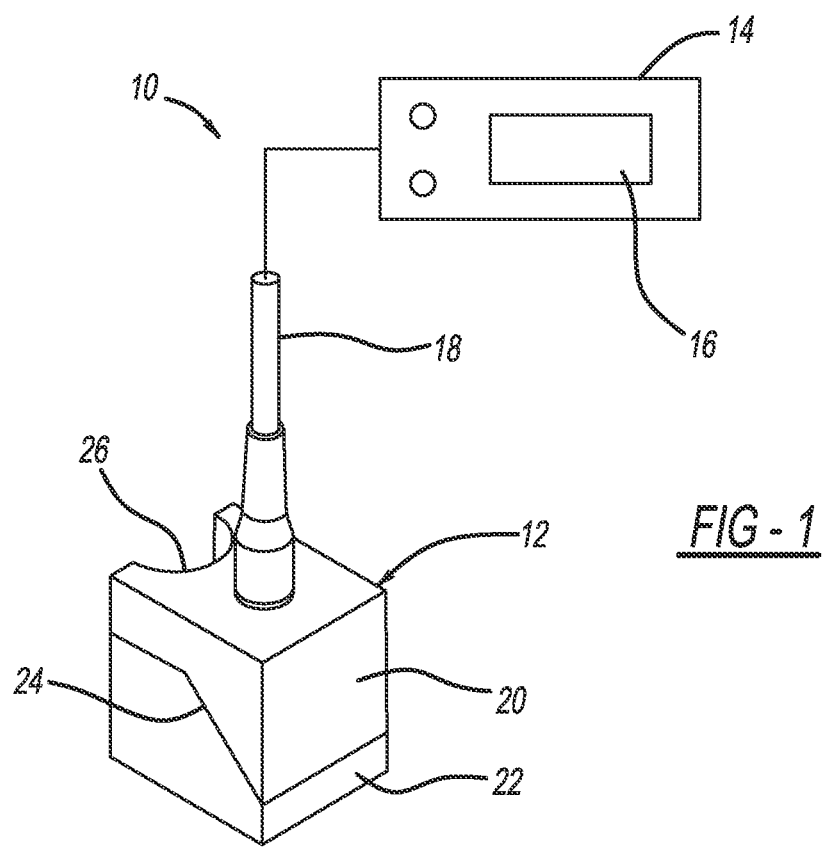
FIG. 1 is an illustration of an inspection system including a phased array transducer and an imaging device.

FIG. 1 is an illustration of an inspection system 10 including a phased array transducer 12 configured to inspect a fastener hole in a structural component without removing the fastener, as will be discussed in detail below. The system 10 also includes a control unit 14 having a display 16 that is electrically coupled to the transducer 12 by a cable 18. The transducer 12 includes a plurality of transducer elements (see FIG. 3) that are electronically pulsed consistent with the discussion herein to scan an ultrasonic beam directed to the component being inspected, and which receives reflected signals from anomalies in the component that can be displayed on the display 16.

The transducer 12 includes an upper housing 20 and a lower housing 22 that are secured together, such as by glue, to have a general rectangular shape. In this non-limiting embodiment, the upper and lower housings 20 and 22 have a general L-shape including a slanted wall 24. The transducer elements are provided in an element housing 28 extending from the upper housing 20 at the wall 24 into the lower housing 22, where the upper housing 20 is generally opaque and the lower housing 22 is generally a clear or translucent support element, such as lucite, that allows the transducer 12 to be easily positioned adjacent to a fastener (see FIG. 2). Further, the housings 20 and 22 include a semi-circular cut-out section 26 that allows the transducer 12 to be partially positioned around the fastener. As will become apparent from the discussion below, the configuration of the housings 20 and 22 can be modified to accommodate different types of fasteners, different sized fasteners, differently spaced apart fasteners, etc.

Figure 2:
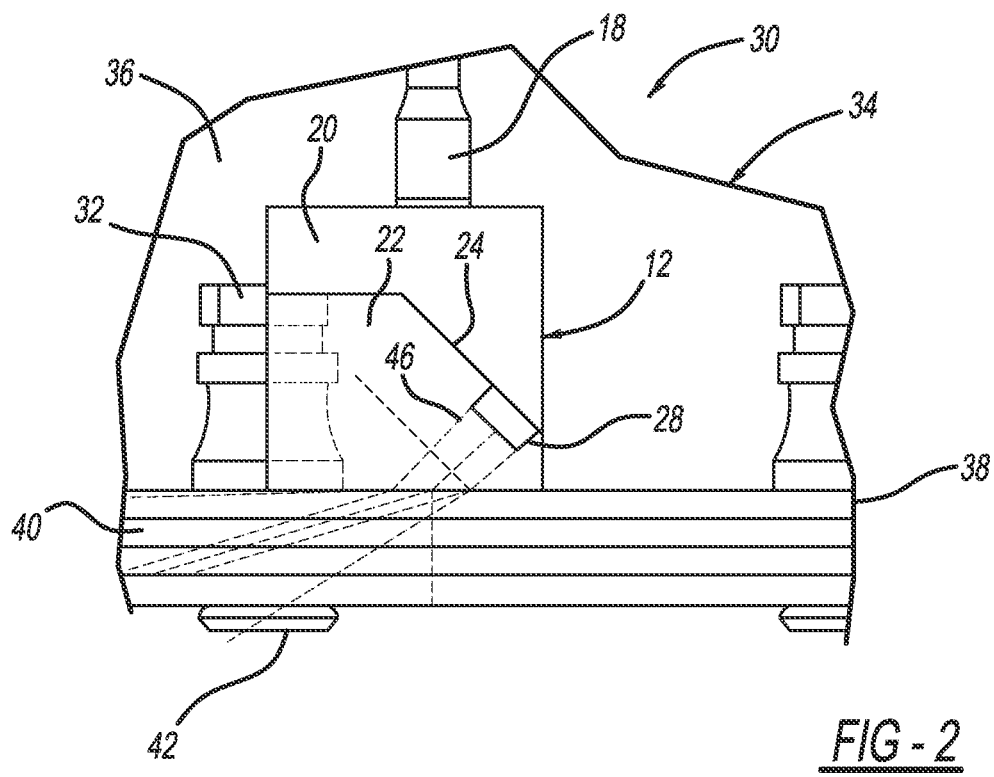
FIG. 2 is a side view of the phased array transducer shown in the system in FIG. 1 and being positioned relative to a fastener coupled to a structure.

FIG. 2 is an illustration 30 showing the transducer 12 inspecting a fastener hole, and surrounding area, in which is positioned a high-lock fastener 32, where the fastener 32 is one of a plurality of fasteners being inspected. In this example, the fasteners 32 are being used to secure a multi-layer keel beam 34 for an aircraft. Particularly, the aircraft keel beam 34 includes a vertical portion 36 extending into the aircraft and a horizontal portion 38. The horizontal portion 38 includes a plurality of layers 40, where a suitable sealant (not shown) is provided between the layers 40 for corrosion mitigation and fluid retention purposes. The fasteners 32 extend through the layers 40 to help secure the layers 40 together, where an outer locking nut 42 is coupled to the fastener 32 external to the aircraft.

The transducer 12 is shown positioned adjacent to the fastener 32 so that part of the fastener 32 is positioned in the cut-out section 26, where the part of the fastener 32 positioned within the cut-out section 26 is shown by dotted line to illustrate that the lower housing 22 is translucent. The transducer elements within the element housing 28 emit ultrasonic beams 46 that are reflected off of the various structures, layers, anomalies, defects, etc., and the reflected signals are received by the transducers elements to provide an image in a manner well understood by those skilled in the art. The beams 46 can be scanned electronically without moving the transducer 12 and can be swept through a wide volume of material at very high speed. Typically, ultrasonic transducer elements require a coupling medium between the transducer elements and the structure being inspected so that the ultrasonic signal is properly coupled thereto. For the keel beam 34 shown in FIG. 2, the existing sealant between the layers 40 operates as such a coupler that allows the signal to be coupled thereto. The coupling action between the layers 40 makes it possible to inspect the entire width of the horizontal portion 38 because the layers 40 ultrasonically act as one piece.

In one non-limiting embodiment, the transducer 12 includes thirty-three transducer elements, where one of the transducer elements is an alignment or centering element for aligning the transducer 12 to the fastener hole, one group of sixteen of the transducer elements inspects one side of the hole and another group of sixteen of the transducer elements inspects an opposite side of the hole when the transducer 12 is properly aligned, which provides the optimal number of elements for the general thicknesses of a random structure. In other transducer designs, fewer or more of the transducer elements may be required for the optimal interrogation of the thickness of the structure. For the alignment procedure, one or more of the beams 46 is reflected from edges of the hole in the vertical portion 38 to identify its center. A desired image will be provided on the display 16 identifying when the transducer 12 is centered to the hole as a calibrated function so that the operator knows that the transducer 12 is properly aligned. In this manner, the hole is interrogated at, for example, the 12:00 o'clock position and the 6:00 o'clock position, and then the transducer 12 is rotated 90°, realigned with the hole and the 3:00 o'clock and 9:00 o'clock positions are scanned so that the entire circumference of the hole is interrogated and inspected.

Figure 3:
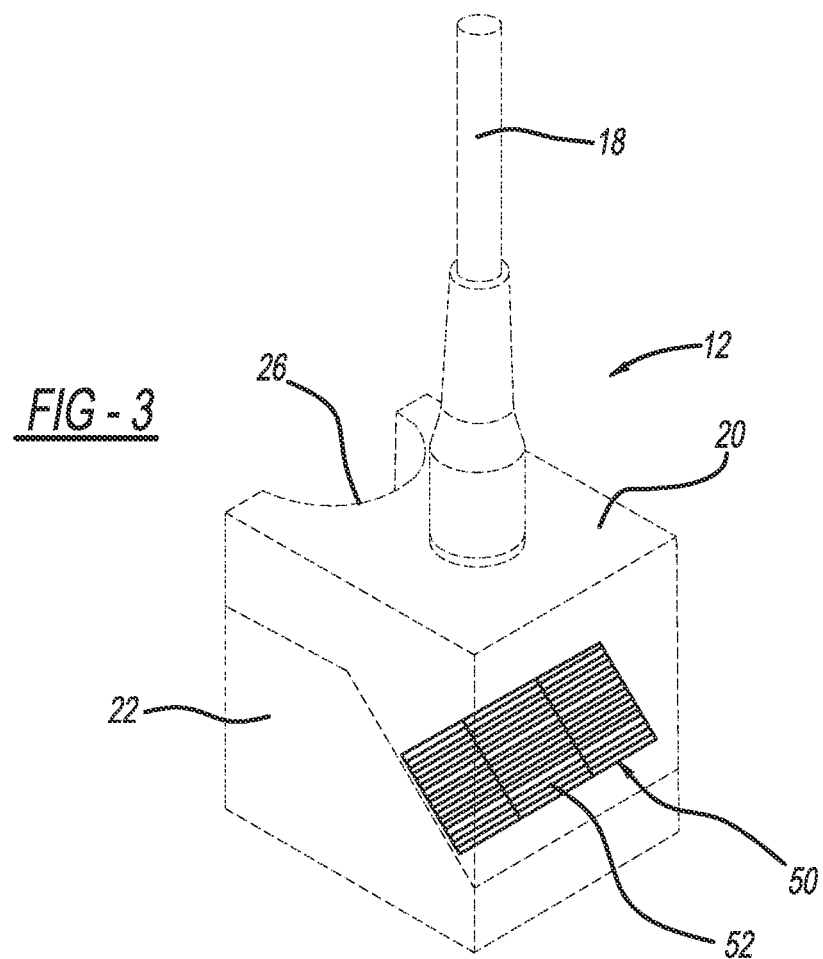
FIG. 3 is an isometric phantom line drawing of the phased array transducer showing transducer elements therein.
Figure 4:
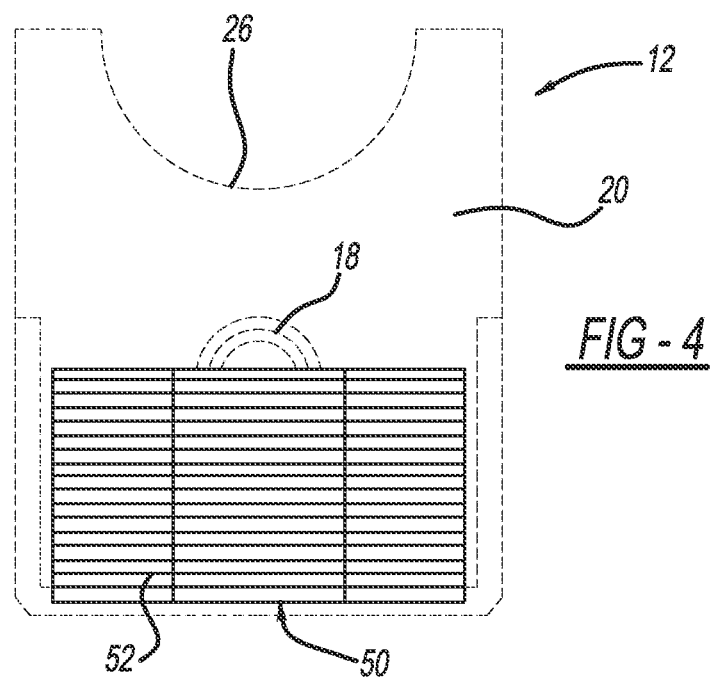
FIG. 4 is a top phantom line drawing of the phased array transducer showing the transducer elements therein.

The array of transducer elements can be configured and positioned within the housing 28 in any suitable manner to provide the desired scan through the entire thickness of the structure. FIG. 3 is an isometric view and FIG. 4 is a top view of the transducer 12 shown in phantom lines so as to depict an array 50 of individual transducer elements 52 therein to show one possible configuration of the transducer elements 52 discussed above. Any suitable group of the transducer elements 52 in the array 50 can be the elements that interrogate one side of the hole, any suitable group of the transducer elements 52 in the array 50 can be the elements that interrogate the opposite side of the hole, and any one or more of the transducer elements 52 can be used to identify the center of the hole for alignment purposes.

A general discussion of the operation of a phased array transducer of the type being discussed herein is given as follows. A phased array transducer contains a number of separate elements in a single housing, where phasing refers to how those elements are sequentially pulsed. A phased array transducer is normally based around a specialized ultrasonic transducer that contains individual transducer elements, such as from 16 to 256 elements, that can be pulsed separately in a programmed pattern. These transducers can be used with various types of wedges, in a contact mode, or in emerging testing. The transducer shape maybe designed to accommodate the installation, such as square, rectangular or round, with test frequencies commonly in the range from 1 to 10 MHz.

The transducer elements in a phased array transducer are generally pulsed in a sequential manner to provide the system phasing. Each pulsed signal from a transducer element is reflected off anomalies and layers and is received by the transducer element, where the signal is conditioned and displayed in a well known manner. The ultrasonic controller records the fundamental parameters of the return signal, namely, its amplitude and where in time it occurs with respect to when the pulse is sent. The transit time is correlated to the depth or distance that the signal is reflected, and the sound velocity of the material. The most basic presentation of the ultrasonic wave form data is an A-scan or waveform display in which return signal amplitude and transit times are plotted on a simple grid with the vertical axis representing amplitude and the horizontal axis representing time. An angular sectorial scan uses thick apertures and steers the beam through a sequential of angles. The transducer may employ a plastic wedge to increase the incident beam angle for generation of shear waves, most commonly in the refracted angle range of 30°-70°. With a linear sectorial scan, the image presentation is a cross-sectional picture of the inspected area of the structure. The operator defines the start angle, end, and step resolution to generate the sectorial image. The aperture remains constant, with each defined angle generating a corresponding beam with characteristics defined by the aperture, frequency and damping. The waveform response from each angle is digitized and plotted relative to color at the appropriate corresponding angle, thus building a cross-sectional image. The sectorial scan is produced in real time so as to continually offer dynamic imaging with transducer movement. This is very useful for defect visualization and increases the probability of detection, especially with respect to randomly oriented defects, utilizing many inspection angles at once.

Fasteners come in a variety of sizes and types, structures come in a variety of thicknesses and orientations, the spacing between fasteners can be close or far apart, etc. In order to accommodate for these variations, the transducer 12 can have any suitable size and shape consistent with the scope of the invention as discussed herein.

Figure 5:
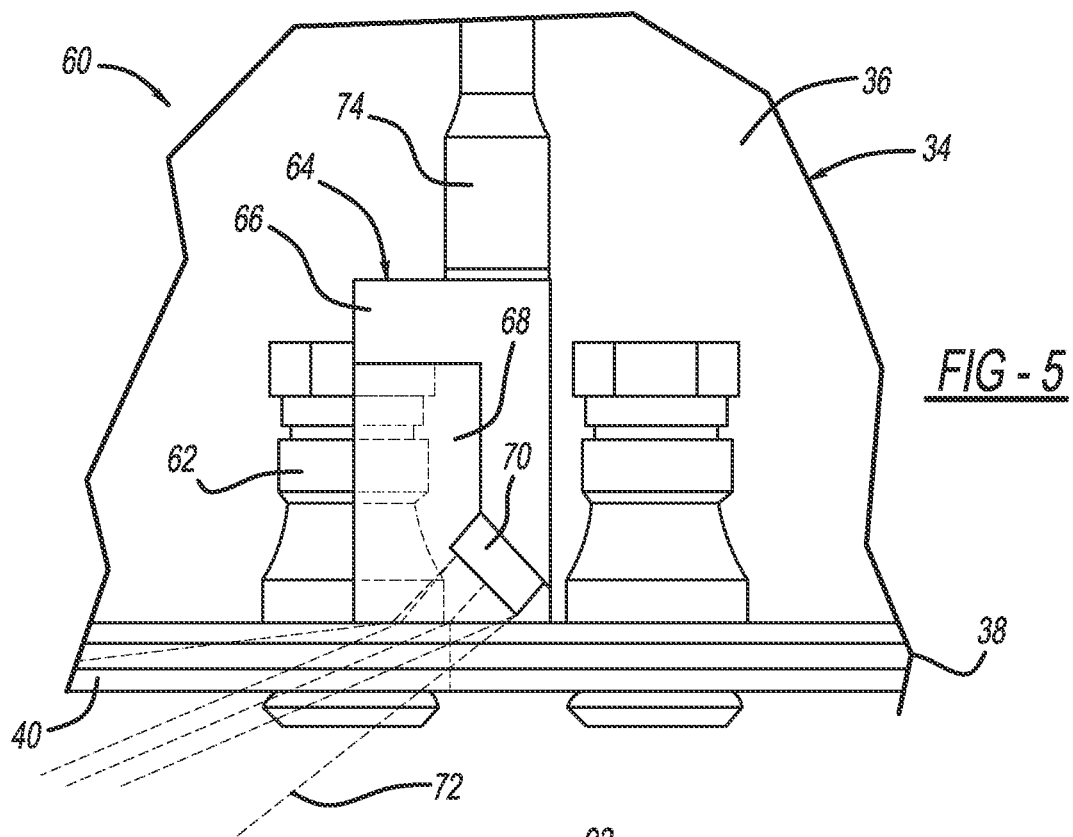
FIG. 5 is a side view of another phased array transducer positioned relative to a fastener having a different size than the transducer shown in FIG. 2.

FIG. 5 is an illustration 60 similar to the illustration 30, where like elements are identified by the same reference number. In this illustration, fasteners 62 are employed to secure the layers 40 that are closer together and are smaller in size than the fasteners 32. In one specific embodiment, the fasteners 62 are three quarters of an inch apart from each other. In order to accommodate the size and spacing of the fasteners 62, a smaller phased array transducer 64 is employed, as shown. As with the transducer 12, the transducer 64 includes an upper housing 66, a lower housing 68, a transducer element housing 70 including a plurality of transducer elements emitting ultrasonic beams 72 and a cable 74. The transducer 64 still includes thirty-three of the transducer elements 52 possibly configured in the same manner as shown in FIGS. 3 and 4 so as to provide the desired beam scanning for typical structure thicknesses.

It is sometimes necessary for a worker performing the component inspection to lie down underneath the component being inspected, such as the keel beam of an aircraft. In order to eliminate the need to hold the phased array transducer in place in this orientation, the present invention proposes a phased array transducer design that includes a magnet that allows the transducer to be held in place by being magnetically coupled to the component being inspected.

Figure 6:
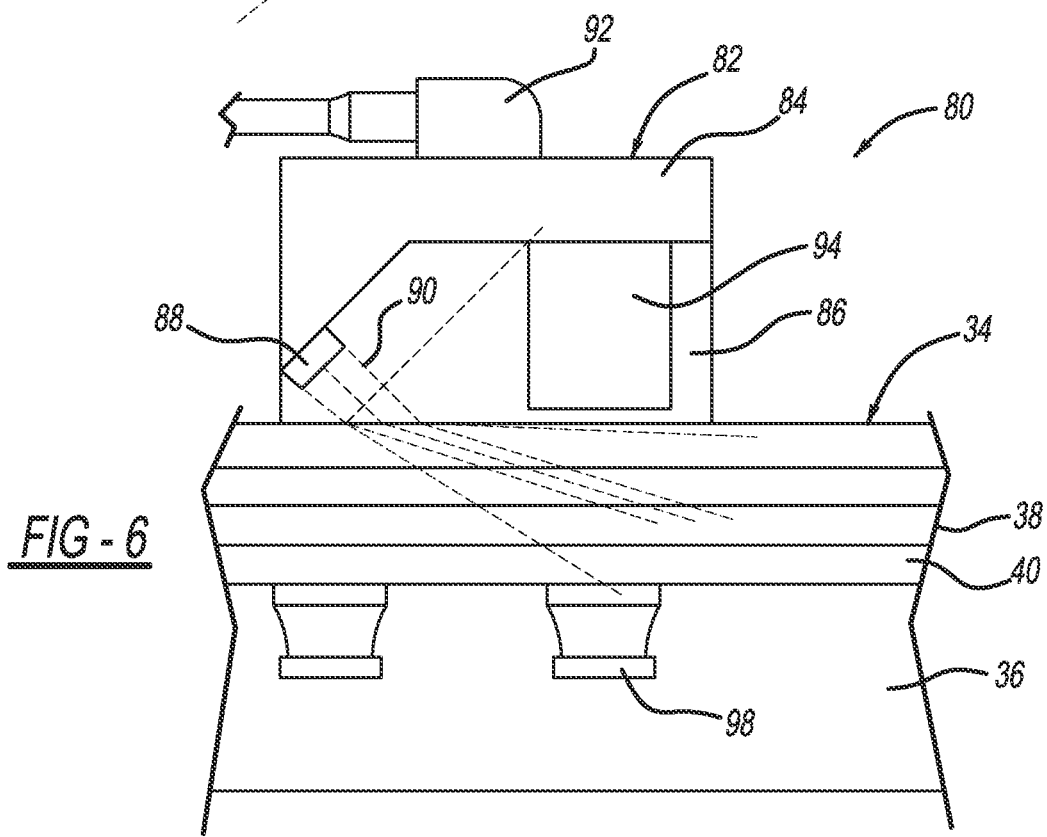
FIG. 6 is a side view of another transducer including a magnet.

FIG. 6 is an illustration 80 that is similar to the illustration 30, where like elements are identified by the same reference number, and shows a phased array transducer 82 similar to the transducer 12. Particularly, the transducer 82 includes an upper housing 84, a lower translucent housing 86, a cable 92, and a transducer element housing 88 from which are emitted ultrasonic beams 90. In this design, the cut-out section 26 is eliminated in the upper and lower housings 84 and 86, and a magnet 94 is positioned within the lower housing 86 that allows the transducer 82 to be magnetically attached to the structure being inspected. In the illustration 80, the structure being inspected is the aircraft keel beam 34, however, the transducer 82 is positioned outside of the beam 34 instead of inside of the beam 34, as was shown in the illustrations 30 and 70. A different type of fastener 98 is used in the illustration 80 to secure the layers 40 together. One transducer element is still used to align the transducer 82 to the hole through which the fastener 98 extends, but the alignment to the hole is done from an opposite orientation.

In an alternate embodiment, the magnet 94 is used to center the transducer 82 instead of using the transducer element, where the magnet 94 is coupled to the fastener 98 so as to properly align the transducer 82. In this embodiment, the centering transducer element can be eliminated.

The foregoing discussion discloses and describes merely exemplary embodiments of the present invention. One skilled in the art will readily recognize from such discussion and from the accompanying drawings and claims that various changes, modifications and variations can be made therein without departing from the spirit and scope of the invention as defined in the following claims.

What is claimed is:

1. A phased array transducer for inspecting a fastener hole and adjacent structure without removing a fastener from the hole, said transducer comprising:
    a body including an upper body portion and a lower body portion; and
    a plurality of transducer elements positioned in the body, wherein at least one of the transducer elements is a centering transducer element that locates the center of the hole or fastener, said plurality of transducer elements also including two groups of inspection transducer elements, where a first group of the inspection transducer elements inspects one side of the hole and a second group of the inspection transducer elements inspects an opposite side of the hole, wherein the body includes a semi-circular cut-out section configured to enclose a portion of the fastener so that the plurality of transducer elements are positioned adjacent to one side of the fastener.

2. The transducer according to claim 1 wherein the lower body portion is made of a clear or translucent plastic.

3. The transducer according to claim 1 wherein the body is rectangular.

4. The transducer according to claim 1 wherein the plurality of inspection transducer elements is thirty-two transducer elements, where the first group of inspection transducer elements is sixteen elements and the second group of inspection transducer elements is sixteen elements.

5. The transducer according to claim 1 further comprising a magnet positioned in the lower body portion.

6. The transducer according to claim 1 wherein the body has a size and shape affective for the size of the fastener and spacing between adjacent fasteners.

7. The transducer according to claim 1 wherein the plurality of transducer elements are configured as an array of elements coupled to the upper body portion and extending into the lower body portion.

8. The transducer according to claim 1 wherein the structure is an aircraft structure.

9. A phased array transducer for inspecting fastener holes and adjacent structure without removing a fastener from the hole, said transducer comprising a body and a plurality of transducer elements positioned in the body, said plurality of transducer elements including a first group of inspection elements for inspecting one side of the hole and a second group of inspection elements for inspecting an opposite side of the hole, wherein the body includes a semi-circular cut-out section configured to enclose a portion of the fastener so that the plurality of transducer elements are positioned adjacent to one side of the fastener.

10. The transducer according to claim 9 wherein the plurality of inspection transducer elements is thirty-two transducer elements, where the first group of inspection elements is sixteen elements and the second group of inspection elements is sixteen elements.

11. The transducer according to claim 9 wherein at least one of the transducer elements is a centering transducer element that locates the center of the hole or fastener.

12. The transducer according to claim 9 wherein the body is rectangular.

13. The transducer according to claim 9 further comprising a magnet positioned in the body.

14. The transducer according to claim 9 wherein the structure is an aircraft structure.

15. A phased array transducer for inspecting fastener holes and adjacent structure without removing a fastener from the hole, said transducer comprising:
   a body including an upper opaque body portion and a lower translucent body portion, said body including a semi-circular cut-out section configured to enclose a portion of the fastener;
   a cable extending from a top surface of the upper body portion; and
   a plurality of transducer elements configured as an array of elements coupled to the upper body portion and extending into the lower body portion, said transducer elements including at least one centering transducer element that locates the center of the hole or fastener, a first group of sixteen inspection transducer elements for inspecting one side of the hole and a second group of sixteen inspection transducer elements for inspecting an opposite side of the hole, wherein the plurality of transducer elements are positioned adjacent to one side of the fastener.

16. The transducer according to claim 15 further comprising a magnet positioned in the lower body portion.

17. The transducer according to claim 15 wherein the body has a size and shape affective for the size of the fastener and spacing between adjacent fasteners.

18. The transducer according to claim 15 wherein the structure is an aircraft structure.

* * * * *